United States Patent
Londt et al.

(10) Patent No.: US 6,865,250 B2
(45) Date of Patent: Mar. 8, 2005

(54) HIGH PITCH CARDIAC HELICAL SCAN WITH EXTENDED RECONSTRUCTION WINDOWS

(75) Inventors: John Londt, Fort Wayne, IN (US); Darin Okerlund, Muskego, WI (US); Tin-Su Pan, Brookfield, WI (US)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 249 days.

(21) Appl. No.: 10/248,171

(22) Filed: Dec. 23, 2002

(65) Prior Publication Data

US 2004/0120446 A1 Jun. 24, 2004

(51) Int. Cl.[7] .................................................. A61B 6/00
(52) U.S. Cl. ............................................. 378/8; 378/62
(58) Field of Search ........................... 378/4, 8, 15, 19, 378/62, 95, 901; 600/425, 428; 382/131

(56) References Cited

U.S. PATENT DOCUMENTS

| | | | |
|---|---|---|---|
| 6,324,247 B1 | 11/2001 | Besson | 378/15 |
| 6,438,196 B1 * | 8/2002 | Cesmeli | 378/8 |
| 6,628,742 B2 * | 9/2003 | Pan et al. | 378/8 |
| 2002/0118790 A1 | 8/2002 | Pan et al. | 378/8 |
| 2002/0136350 A1 | 9/2002 | Pan et al. | 378/8 |

FOREIGN PATENT DOCUMENTS

| | | | | |
|---|---|---|---|---|
| EP | 0 983 747 A1 | 3/2000 | | A61B/6/03 |
| EP | 1 095 619 A1 | 5/2001 | | A61B/6/00 |

* cited by examiner

Primary Examiner—David V. Bruce
Assistant Examiner—Courtney Thomas
(74) Attorney, Agent, or Firm—Cantor Colburn LLP

(57) ABSTRACT

A method for image reconstruction and reducing patient dose, and an imaging system for accomplishing these methods, includes selecting a primary phase of a cardiac cycle and calculating compromised phase regions based on a selected compromised phase value. If the image position is located within the primary phase, then an image is generated at the primary phase. If the image position is not located within the primary phase, but is located within a compromised phase region, then an image is generated at the compromised phase region.

25 Claims, 8 Drawing Sheets

Left, center, and right locations

FIG. 9

Compromised phase region

HIGH PITCH CARDIAC HELICAL SCAN WITH EXTENDED RECONSTRUCTION WINDOWS

BACKGROUND OF THE INVENTION

This invention relates to methods and apparatus for reconstruction of computed tomography ("CT") images, and more particularly, this invention relates to methods and apparatus for reducing patient dose during cardiac imaging.

In at least one known computed tomography ("CT") imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the object being scanned is not moved, and the projection data is processed to construct an image that corresponds to a two dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

Helical scanning is used in some CT imaging systems, as are multislice detectors. During helical scans, a patient is placed on a moving table, which transports the patient through an opening in the rotating gantry. The direction of movement is referred to as the z-axis of the imaging system, and a multislice detector of such a system has multiple parallel rows of detector elements. The rows themselves are stacked in the z-direction, so that projection data acquired by each row corresponds to a "slice" of a patient. For axial scans, the plane of each slice is perpendicular to the z-axis if an axial scan is performed. The detector elements of adjacent rows of known multislice detector arrays abut one another, and are characterized by a spacing distance between their centers. When a helical scan is performed, the table moves a selectable distance during one gantry rotation. The ratio of the z-axis movement during one gantry rotation to the z-axis spacing between centers of the detector elements in each row is defined as the "helical pitch" that characterizes a given scan. (For a single row detector array, the z-axis spacing is replaced by the thickness of the single row in the z-axis direction).

During a helical scan, projection data is collected during transport of the patient through the rotating gantry. With appropriate image reconstruction techniques, helical scans provide a relatively efficient way of imaging a volume of a patient that is thicker along the z-axis than the combined thickness of the rows of a multislice detector.

In some CT imaging applications such as cardiac imaging, a body part being imaged is not stationary. In the cardiac imaging case, it is necessary to use EKG gating to reconstruct images with data from a particular phase of a cardiac cycle. However, imaging an entire heart typically requires scanning a patient volume having a thickness of 12 cm, which is quite large in relation to the total thickness that can be imaged by known multislice CT detector arrays. In addition, projection data from a sufficient span of view angles is required for CT image reconstruction of any selected cardiac cycle phase. These requirements work to reduce the maximum helical pitch that can be used for cardiac scanning. However, with a low pitch helical scan, it may be difficult for a patient to hold his or her breath long enough during the scan to avoid additional body movement that would reduce the resolution of reconstructed images. Also, because low pitches translate directly into longer scanning times, patient dose is increased.

Figure 1:
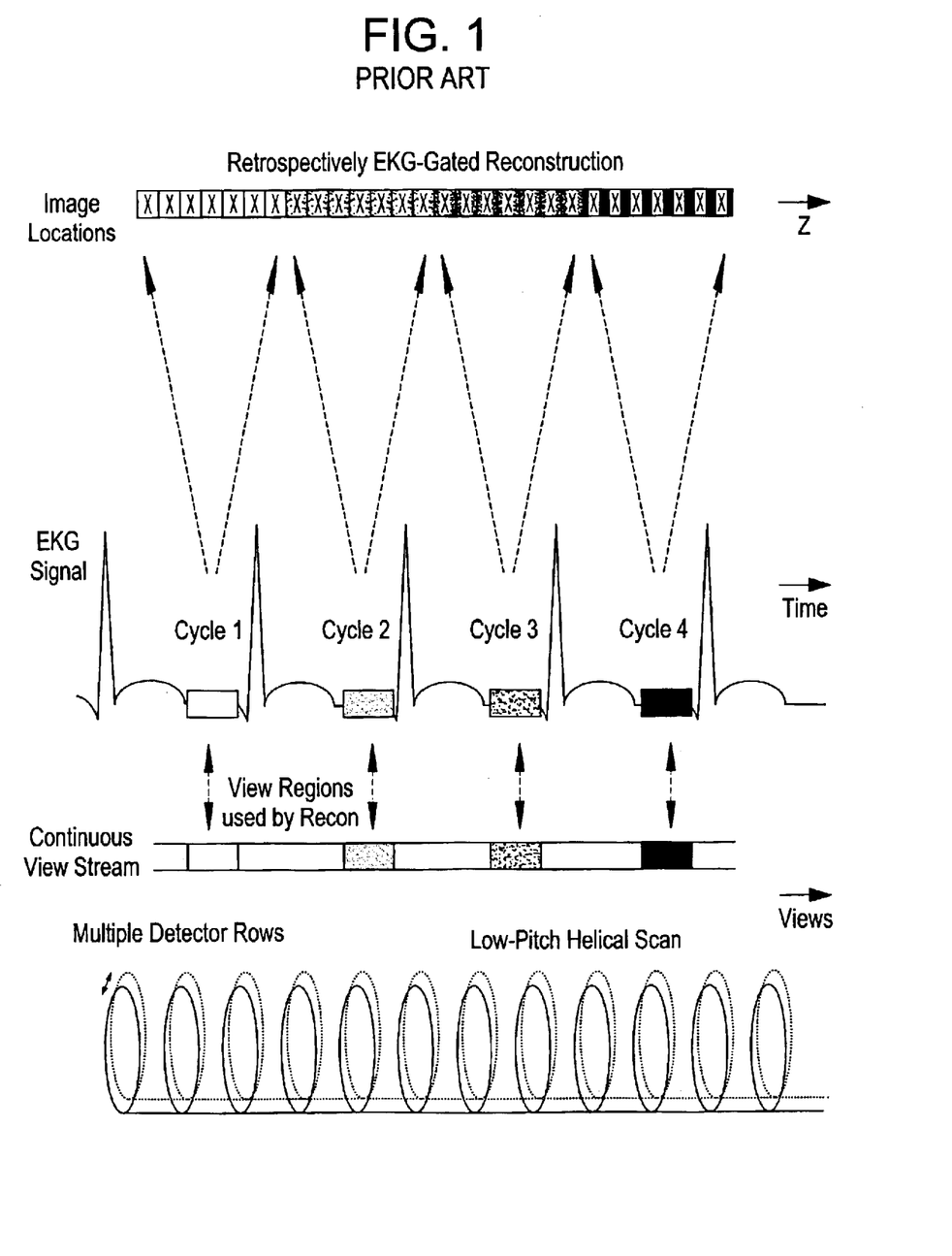
FIG. 1 shows a diagram of prior art EKG gated reconstruction.

FIG. 1 shows an overview of EKG-gated reconstruction. It depicts the basics of reconstructing EKG-gated images from a helical scan. Images are generated from regions of the continuous view stream called cardiac cycles. These cycles are chosen using the EKG signal to reduce the amount of motion artifact in the images. It should be noted that the low-pitch helical scan provides for a continuous view stream, but only selected regions of the continuous view stream, those regions which correspond to a low motion condition of the heart, are utilized for image reconstruction.

Figure 2:
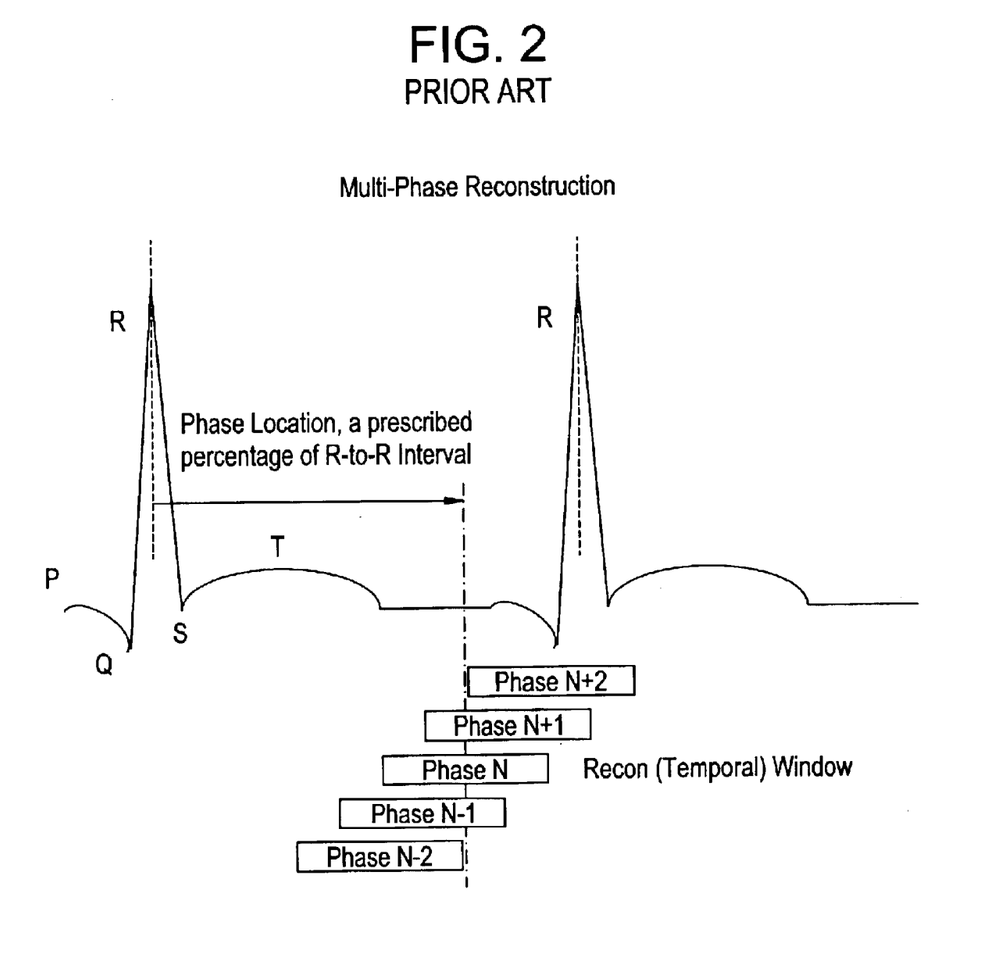
FIG. 2 shows a diagram of prior art phase location for gated construction.

FIG. 2 shows a cardiac cycle of an EKG signal waveform, including a systole condition, or period, and a diastole condition, or period, of the heart. The portions of the EKG signal labeled Q, R and S are referred to as the QRS complex, in which the R-feature, or R-wave, is the most prominent, highest amplitude, feature of the entire EKG signal. The cardiac cycle is typically defined as beginning with an R-wave and continuing until the occurrence of a next R-wave. EKG gating selects times when a best image of the heart is available. An EKG machine is connected to a patient. A cardiac cycle period is determined, for example, as a time between R-peaks of the EKG. Using an R-peak as a reference and the determined cardiac cycle period, image acquisition during a scan is gated so that image data is acquired only during periods of a cardiac cycle for which the heart is nearly stationary. FIG. 2 shows the phase location of gated-reconstruction within the R-to-R interval. It shows how a recon window shifts along the EKG waveform as the window's phase is increased or decreased. Note that allowing the phase to change may move the recon window into an area where there may be more motion, such as the systolic phase.

The current cardiac helical scan protocol and algorithm are optimized for precise cardiac phase location and not for acquisition time or dose reduction. Other problems with the algorithm occur when a patient's heart rate slows significantly during a cardiac scan or if a technician prescribes an incorrect pitch or if the EKG gating software does not detect a R-peak properly. If one of these problems occurs there may be gaps in the cardiac data for a given R-to-R phase and the images generated in these data gaps are currently not ECG gated and generally have poor image quality in that the motion of the heart is not frozen.

BRIEF SUMMARY OF THE INVENTION

The above discussed and other drawbacks and deficiencies are overcome or alleviated by a method of reconstructing cardiac images including receiving information selecting a primary phase within a cardiac cycle, receiving information selecting a phase compromise value, calculating compromised phase regions using the phase compromise value, determining whether an image position is within the primary phase, generating an image at the primary phase if the image position is within the primary phase, and generating an image at a compromised phase if the image position is not within the primary phase but is within the compromised phase regions.

In another embodiment, a computed tomographic imaging system for reconstructing cardiac images including a plurality of detector rows and a rotating gantry is configured to scan a patient at a selected helical scanning pitch, acquire projection data of the patient, including the patient's heart, from the plurality of detector rows, accept a primary phase of a cardiac cycle of the patient for image reconstruction where the heart is more motionless than at other portions of the cardiac cycle, calculate a compromised phase, and reconstruct images at the primary phase when the image locations are within the primary phase, and reconstruct images at the compromised phase if position of the image locations is not within the primary phase but is within the compromised phase.

In another embodiment, a storage medium encoded with machine-readable computer program code for reconstructing cardiac images includes instructions for causing a computer to implement a method including receiving information selecting a primary phase within a cardiac cycle, receiving information selecting a phase compromise value, calculating compromised phase regions using the phase compromise value, determining whether an image position is within the primary phase, generating an image at the primary phase if the image position is within the primary phase, and generating an image at a compromised phase if the image position is not within the primary phase but is within the compromised phase regions.

In another embodiment, a computed tomographic imaging system for reconstructing cardiac images, the imaging system having a plurality of detector rows and a rotating gantry, includes means for scanning a patient at a selected helical scanning pitch, means for acquiring projection data of the patient, including the patient's heart, from the plurality of detector rows, means for accepting a primary phase of a cardiac cycle of the patient for image reconstruction where the heart is more motionless than at other portions of the cardiac cycle, means for calculating a compromised phase, and means for reconstructing images at the primary phase when the image locations are within the primary phase, and means for reconstructing images at the compromised phase if position of the image locations is not within the primary phase but is within the compromised phase.

In another embodiment, a method of reconstructing cardiac images using a computed tomographic imaging system includes receiving information selecting a primary phase within a cardiac cycle, receiving information selecting a phase compromise value, calculating compromised phase regions using the phase compromise value, selecting a helical scanning pitch for scanning a patient, scanning the patient, including the patient's heart, with a computed tomographic imaging system having a plurality of detector rows and a rotating gantry to acquire projection data from the plurality of detector rows, determining whether an image position is within the primary phase, generating an image at the primary phase if the image position is within the primary phase, and generating an image at a compromised phase if the image position is not within the primary phase but is within the compromised phase regions.

In another embodiment, a method of reducing radiation dose delivered to a patient during a computed tomographic imaging session includes increasing a helical scanning pitch for scanning a patient and extending a reconstruction window around a primary phase for image reconstruction.

The above discussed and other features and advantages of the present invention will be appreciated and understood by those skilled in the art from the following detailed description and drawings.

DETAILED DESCRIPTION OF THE INVENTION

Figure 3:
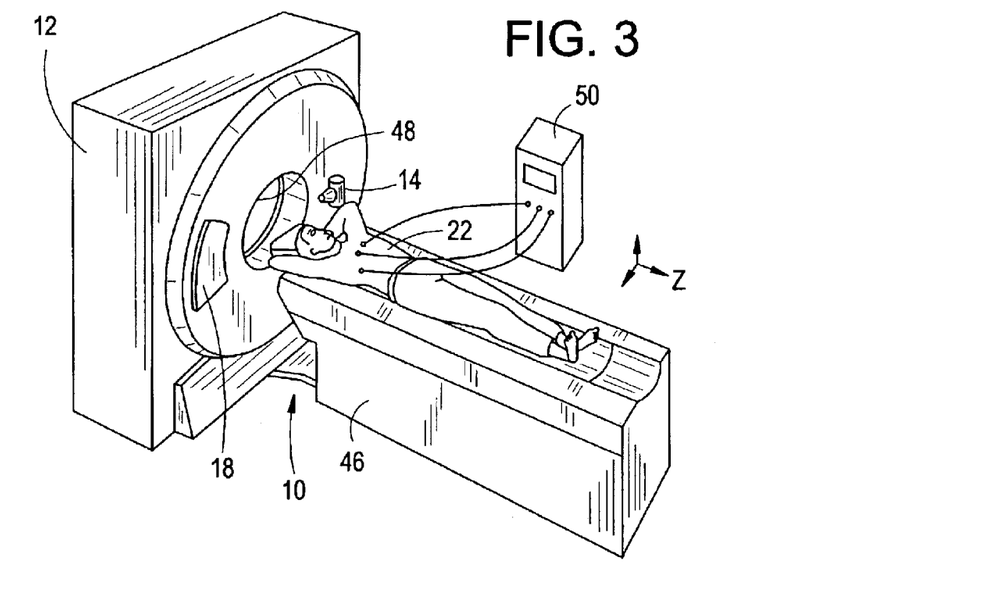
FIG. 3 shows a pictorial view of a CT imaging system.
Figure 4:
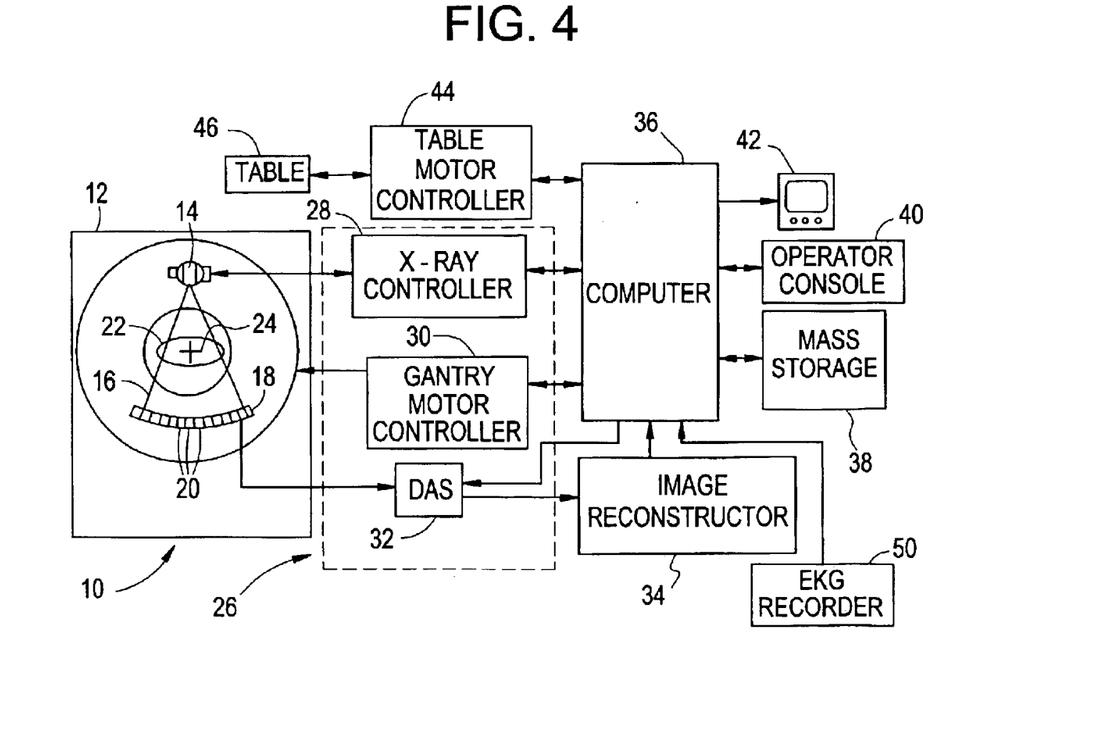
FIG. 4 shows a block schematic diagram of the system illustrated in FIG. 1.

Referring to FIGS. 3 and 4, a computed tomography ("CT") imaging system 10 is shown as including a gantry 12 representative of a "third generation" CT scanner. Gantry 12 has an x-ray source 14 that projects a beam of x-rays 16 toward a detector array 18 on the opposite side of gantry 12 Detector array 18 is formed by detector elements 20 which together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation 24. Detector array 18 may be fabricated in a single slice or multi-slice configuration. In a multi-slice configuration, detector array 18 has a plurality of rows of detector elements 20, only one of which is shown in FIG. 4.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 in gantry 12. Particularly, table 46 moves portions of patient 22 through gantry opening 48. The direction of motion of the table defines the z-axis of imaging system 10. The multiple rows of detector array 18 are stacked in the z-axis direction so that, during an axial scan, projection data is acquired from a number of parallel slices of a volume of patient 22. The parallel slices define planes that are perpendicular in the z-direction, when an axial scan is performed. For a helical scan, a helical pitch is determined that is a function of the selected or default values. The reconstruction then obtains a set of images from the beginning of the scan with the specified or default phase and overlap. The set of images thus reconstructed should cover an entire heart without any gap.

Figure 5:
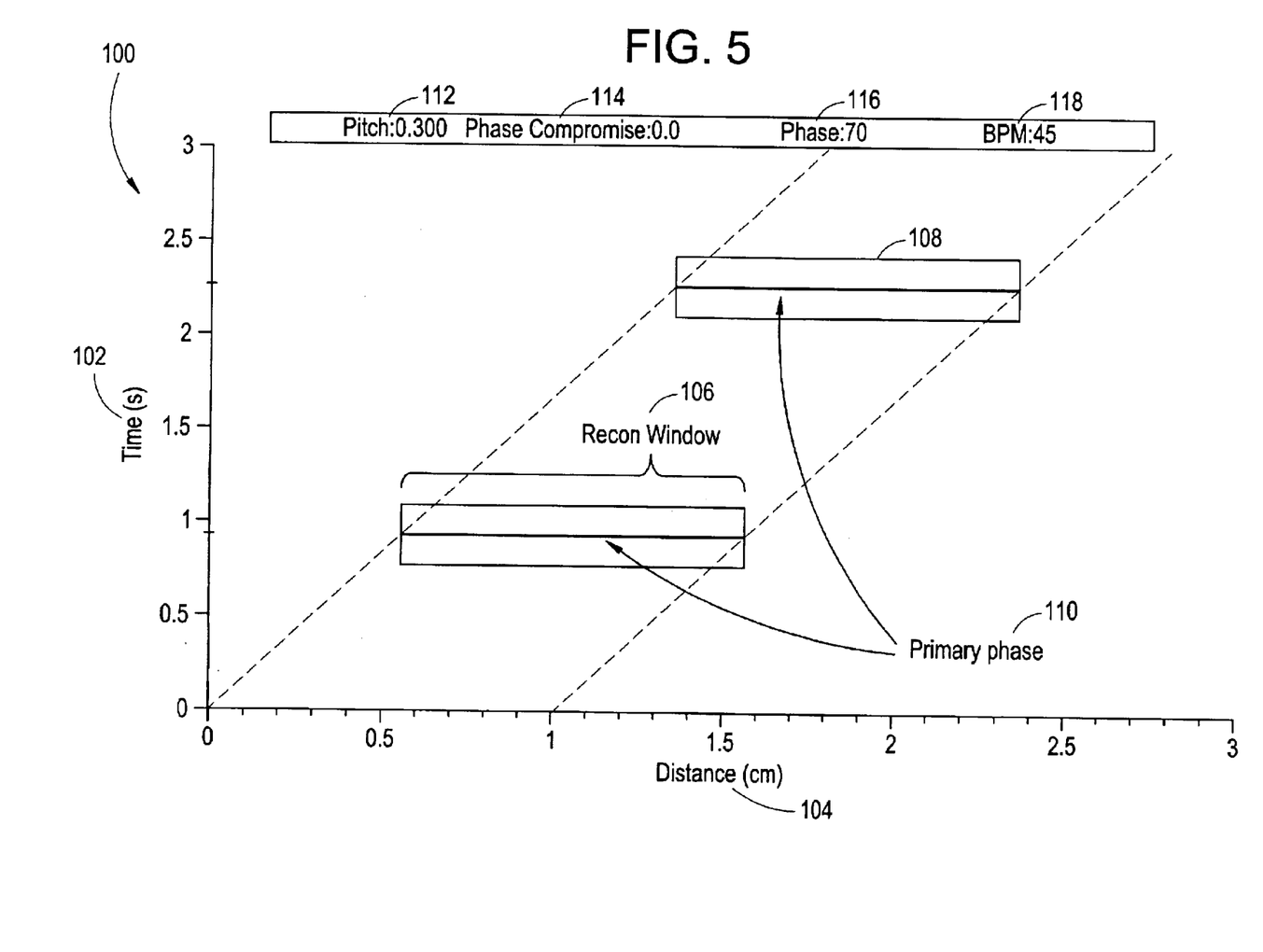
FIG. 5 shows a graph of a cardiac reconstruction algorithm.

As shown in FIG. 5, a graph. 100 shows a plot of the primary phase 110 of reconstruction windows 106, 108 mapped with respect to time vs. distance in the z direction. FIG. 5 demonstrates how the current reconstruction algorithm has considerable overlap of the cardiac reconstruction windows 106, 108, which are the regions that illustrate the distance in z that is covered by each cardiac cycle. Overlapping reconstruction windows is done so that images may be reconstructed as shorter temporal resolution which requires information from two or more overlapping cardiac cycles. Therefore, overlapping reconstruction ("recon") windows are necessary for multisector cardiac recon, such as Snapshot Burst image reconstruction available from GE Medical Systems, but are not necessary for image reconstruction which only uses data from one cardiac cycle to reconstruct an image, such as Snapshot Segment image reconstruction available from GE Medical Systems. The exemplary plot shown in FIG. 5 assumes a pitch of 0.300. The pitch can be defined relative to total x-ray collimation (x), or individual detector width (d), where $x = d1 + d2 + d3 + \ldots + dn$, where n=number of detectors in the x-ray beam width.

$Pitch_x$=table travel/x-ray beam width $Pitch_d$=table travel/detector width

Table travel is measured in the z direction. Although either definition is usable, in this example, pitch is defined in view of full (multislice) detector width, i.e. $Pitch_x$. The exemplary plot shown in FIG. 5 further assumes a phase compromise 14 of 0.0, phase 116 of 70, and beats per minute ("BPM") 118 of the patient to be 45 BPM.

The current algorithm demonstrated by an exemplary result in FIG. 5 may reconstruct images at z-locations beyond the center of the end detectors, which can introduce artifacts into images generated at these locations. The current algorithm does this to increase coverage and because only the images generated at or near the edge of a recon window are affected so that the effects on overall image quality are small.

For the method and algorithm disclosed herein, cardiac scans conducted on patients may be conducted at higher pitches to decrease scan time and dose to patient, particularly for applications such as cardiovascular imaging where there is less motion due to the beating heart. As discussed above, other problems with the prior algorithm occur when a patient's heart rate slows significantly during a cardiac scan or if a technician prescribes an incorrect pitch or if the EKG gating software does not detect an R-peak properly. If one of these problems occurs there may be gaps in the cardiac data for a given R-to-R phase and the images generated in these data gaps are currently not ECG gated and generally have poor image quality in that the motion of the heart is not frozen. The technique disclosed herein improves image quality for images produced in these gaps by producing gated images and it allows patients to be scanned at higher pitches, thereby reducing scan time and patient dose. The new high pitch helical cardiac algorithm also preferably accounts for end detectors and their related artifacts since more images are generated at the edge of a reconstruction window.

Figure 6:
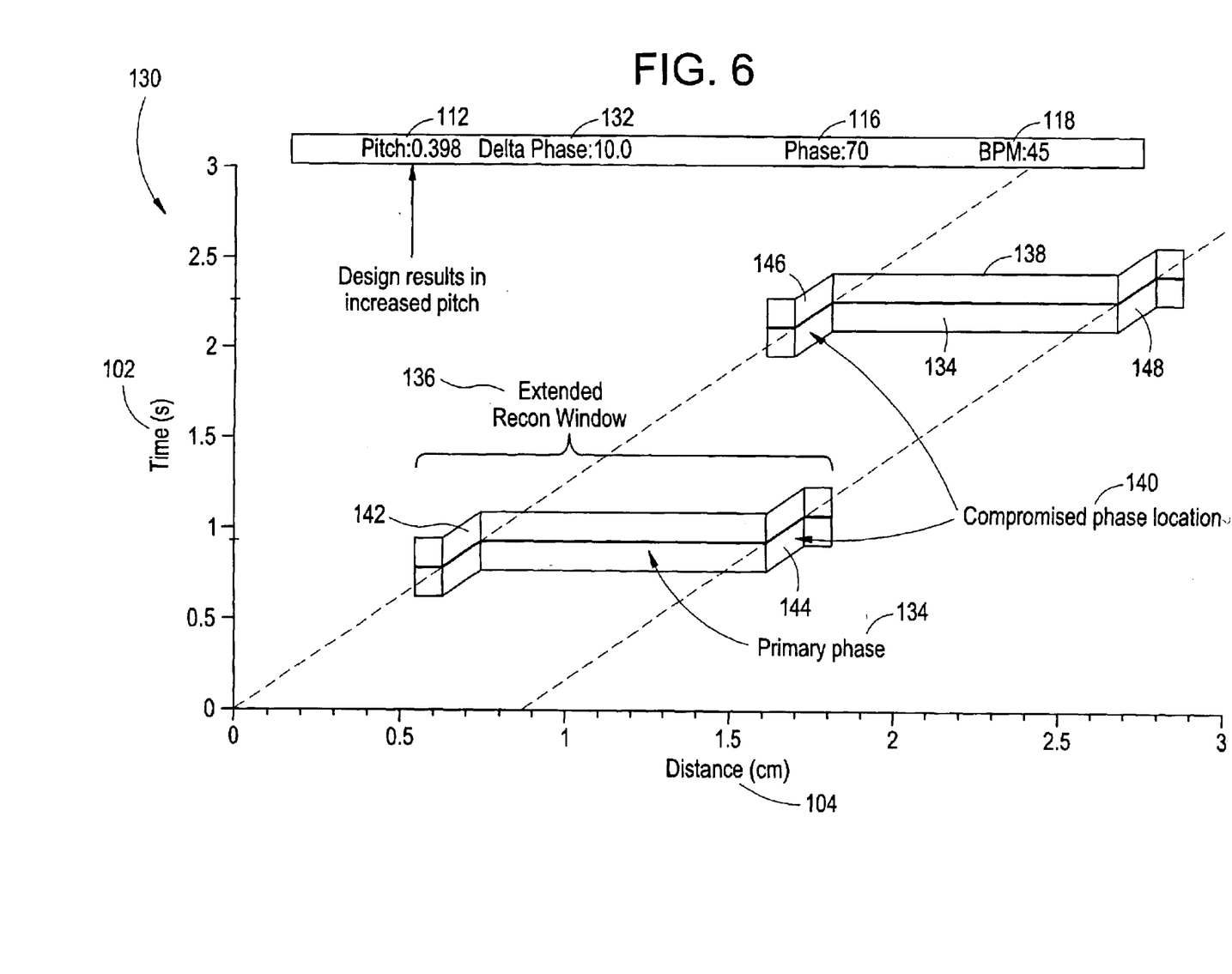
FIG. 6 shows a graph of a cardiac reconstruction algorithm using extended recon windows.

With reference to FIG. 6, the suggested new algorithm, as will be described further below, has considerable advantages over the existing algorithm including the reduction of patient dose. A higher pitch leads to faster scan times which leads to reduced dose, or exposure to x-rays. The revised plot 130 plots extended recon windows 136, 138 with respect to time 102 versus distance 104. The phase 116 is still assumed to be 70, and the BPM 118 is still 45. The pitch 112, however, in FIG. 6 is 0.398 which is considerably larger than the 0.3 which is used by the algorithm shown in FIG. 5. The higher pitch, with the other factors shown in FIG. 6 translates to a dose reduction of approximately 25% (1−current pitch/proposed pitch=$1 - 0.3/0.398 \approx 1 - 0.75 \approx 0.25$) and the dose savings are much greater for higher heart rates and or larger compromises in phase. Delta phase 132 in this example is 10 which refers to allowing 10% more, above and below the target phase location, of the cardiac phase to be selected for possible image reconstruction. By increasing the amount of time the operator is willing to use, the length of each view window is also extended from the continuous view stream as shown in FIG. 1. Thus, some spread in the cardiac phase location (the center of the recon window) is allowed to decrease the overall acquisition time and patient dose. Each extended recon window 136, 138 includes a primary phase 134 and leading and trailing compromised phase locations 140. That is, each extended recon window 136, 138 includes a leading compromised phase 142, 146, respectively, and a trailing compromised phase 144, 148 respectively. The compromised phase regions extend the length of each view window in FIG. 1, however, only a small percentage of images will require any compromise to the specified phase location. Additionally, for those images which do, only a portion of the acquisition data used to make such an image will use data from a slightly compromised phase. As shown in FIG. 6, a small amount of overlap between the recon windows is typically used so that if the patient's heart rate slows during the exam then there will not be a gap in coverage.

The "compromised" phases introduce more cardiac motion in the images by taking images from a broader range in the cardiac cycle. However, an operator is compromising cardiac phase location of the images (and therefore introducing motion into the images) in order to significantly reduce scan time. As an example, consider a 300 ms recon window (determined by speed of the scanner) and a 60 BPM heart rate. Without compromise, data within a 300 ms window will be used to generate a given image. If a 5% phase tolerance (i.e., 75%+/−5% for example), is allowed, then up to an additional 50 ms on each end of the recon window may be allowed yielding a 400 ms temporal window. In practice, for a given image, an operator need only compromise on one end of the window such that the temporal window would be as much as 350 ms in this example.

Figure 8:
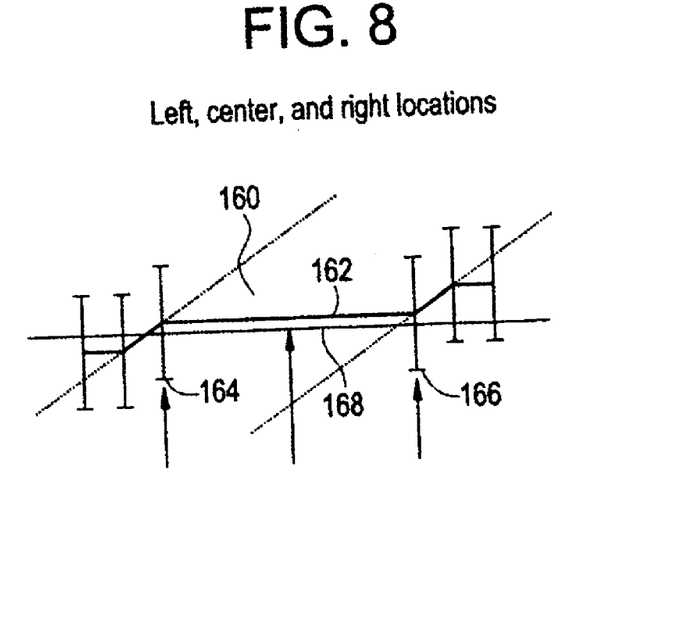
FIG. 8 shows an extended recon window.

FIG. 8 shows one entire recon window. A recon window is basically a graphical representation of where an image may be generated with respect to time and detector location. The height of the box corresponds to the length of time or rotation required to reconstruct one image and the x-direction is the position the image can be generated at and the y-direction is the phase location the images will be generated at. The vertical size of each rectangle represents the temporal window. So the edge of the recon window is the end of each of these boxes. The algorithm also does not generate images beyond the center of the end detectors until the edge of the recon window. This is done so that the images generated at the compromised phase locations will have good image quality. Images generated beyond the middle of the last detector inherently have more noise introduced into the image. Therefore, these images would not be generated until absolutely necessary. The proposed algorithm also makes it possible to almost always generate gated images. The algorithm has back-off logic to enable it to always generate an image regardless of whether it is gated or ungated. Ungated is a last case scenario but could happen if the patient's heart rate slowed to a large enough degree. The new algorithm allows for the minimization of the chance of ungated images being generated during a system exception path (extreme heart rate drop, EKG-lead falls off, etc.) The protocol, on the other hand, should allow for only gated images to be produced. With the existing algorithm it is possible that gaps in the data could occur due to inadequate z-coverage or due to software or operator error, but this algorithm makes it possible to generate gated images by compromising the phase at these locations instead of creating ungated images. Generating gated images in these gaps will improve image quality.

Figure 7:
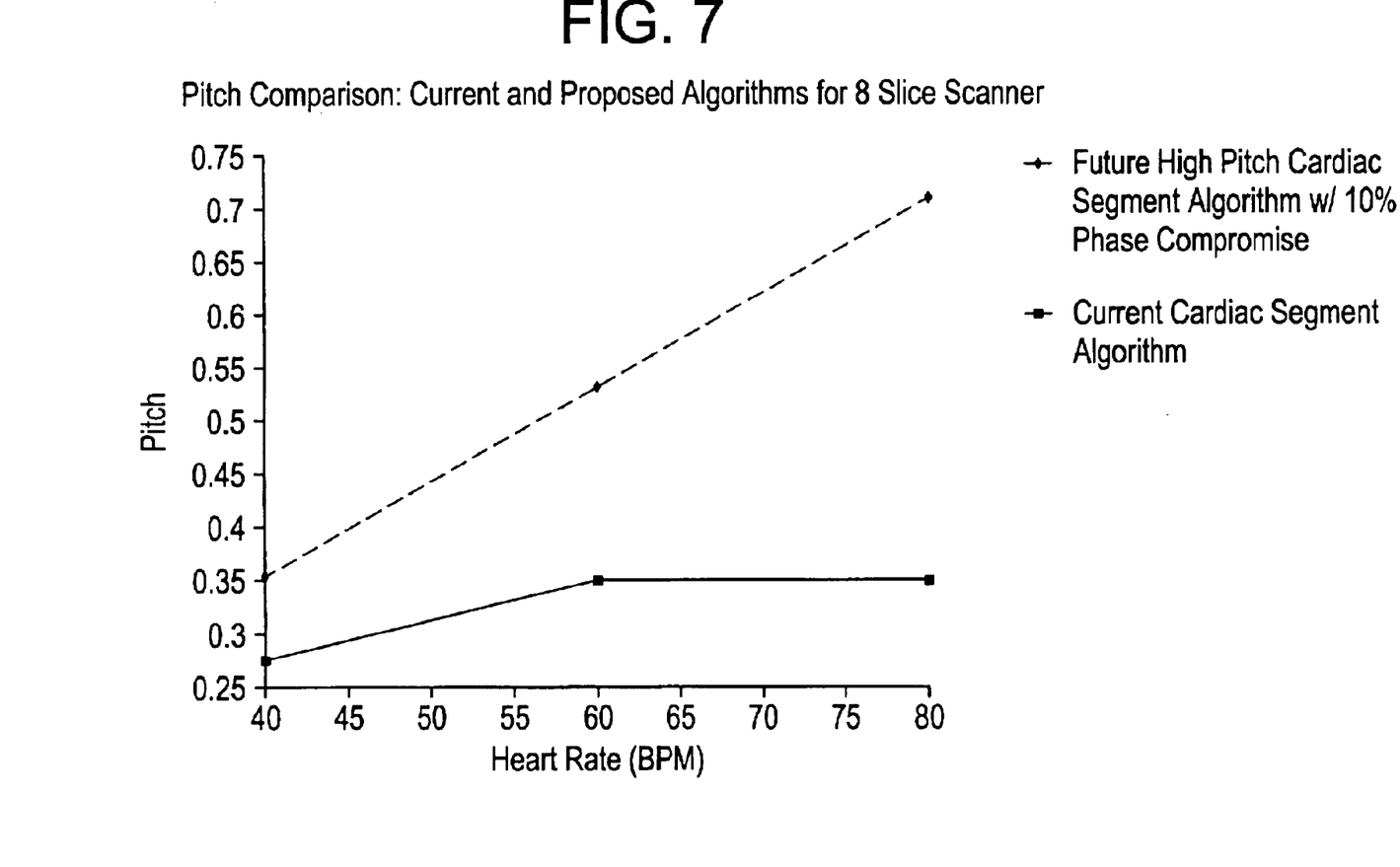
FIG. 7 shows a plot of pitch versus heart rate for two different cardiac segment algorithms.

FIG. 7 graphically depicts the pitch increase that the new high pitch algorithm offers over the current segment recon for an 8-slice scanner. The current algorithm caps the pitch at 60 BPM so that the customer may always retrospectively apply the multisector cardiac recon such as the Snapshot Burst algorithm from GE Medical Systems for heart rates greater than 60. However, with the new algorithm the customer can greatly reduce dose if they do not wish to do Burst reconstruction. For example, there is approximately a 50% dose reduction by using the high pitch algorithm to reconstruct segment images at 80 BPM on an 8-slice system. It should also be noted that as the heart rate is increased, the pitch may also be increased, such as linearly as shown, with the new algorithm.

Figure 9:
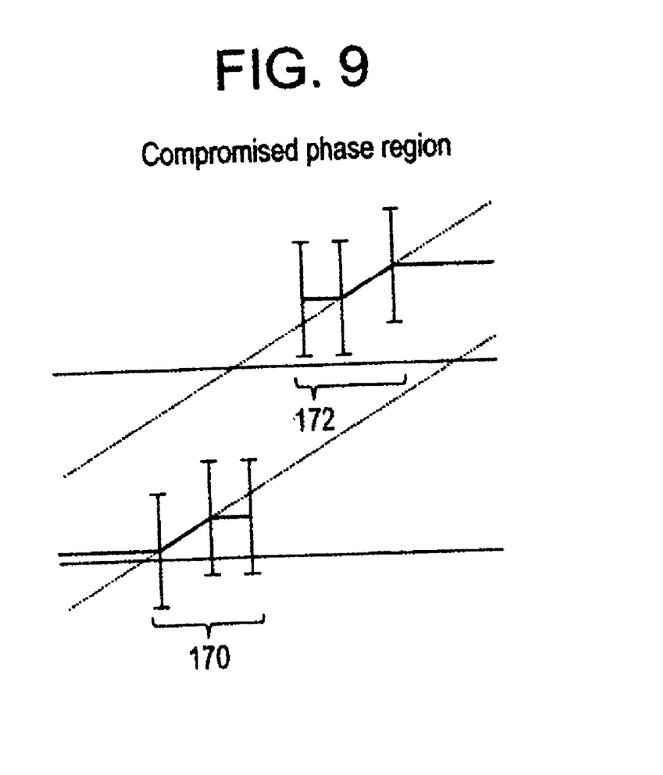
FIG. 9 shows compromised phase regions of extended recon windows.

FIGS. 8 and 9 show extended recon windows 160 as in FIG. 6. Extended recon window 160 includes a primary phase 162 positioned between a left, or first, location 164 and a right, or second, location 166. Center location 168 denotes the center of the primary phase 162 between the left location 164 and the right location 166. Compromised phase region 170 and 172 from two consecutive extended recon windows 160 are shown in FIG. 9. Each extended recon window 160 includes a leading compromised phase region 172 adjacent the left location 164 of the primary phase 162 and a trailing compromised phase region 170 adjacent the right location 166 of the primary phase 162.

Figure 10:
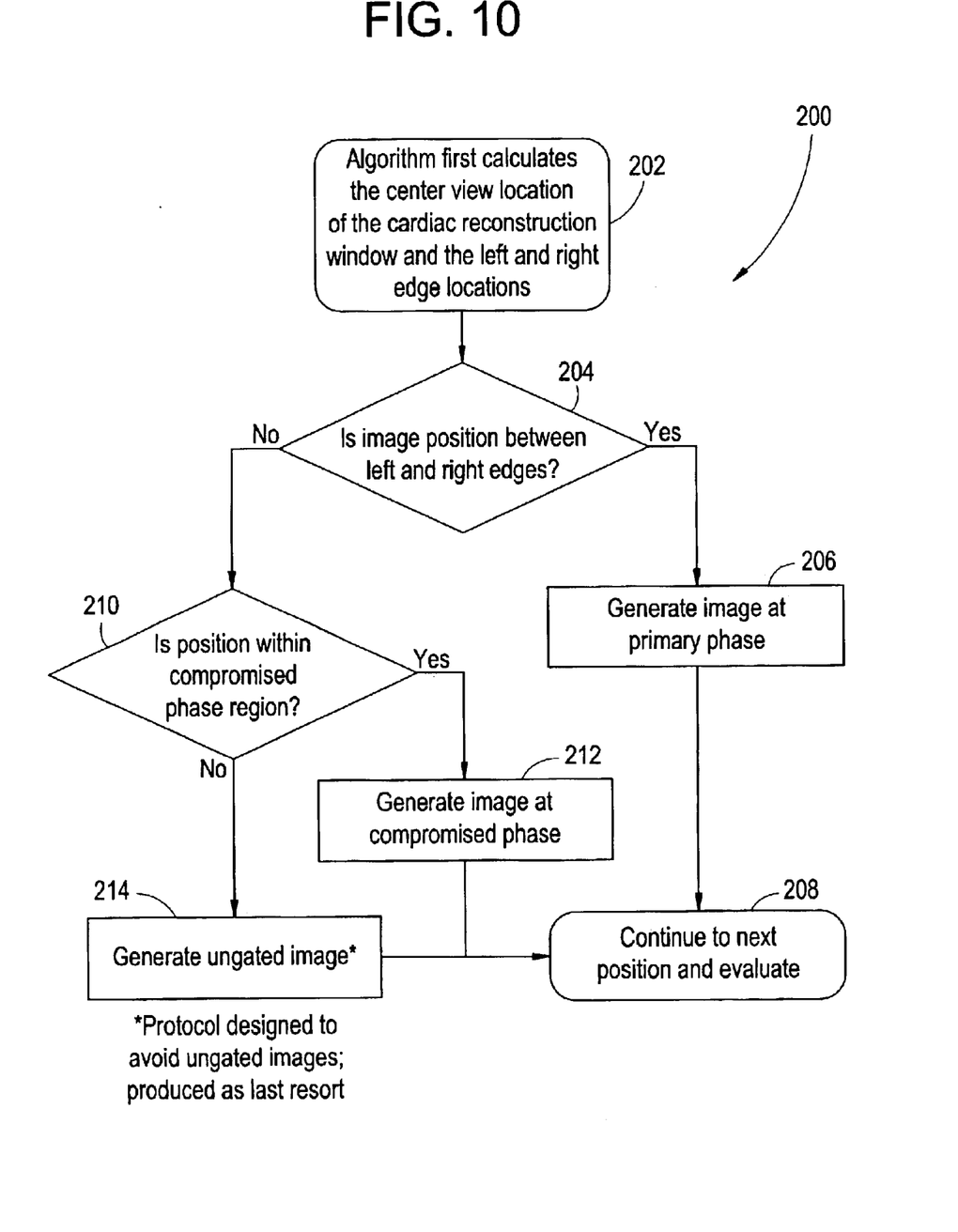
FIG. 10 shows a flow diagram of a cardiac segment algorithm.

Turning now to FIG. 10, a flow diagram of the algorithm 200 is shown. As shown in FIG. 10, and with reference to FIGS. 8 and 9, block 202 demonstrates how the algorithm 200 first calculates the center view location 168 of the cardiac reconstruction window and the left and right edge locations 164, 166. In block 204, the algorithm 200 determines if the image position is between the left and right edges 164, 166. If the answer is yes, then the algorithm proceeds to block 206 where an image is generated at the primary phase. The algorithm then proceeds to block 208 where the method continues to the next position (the position is the z-position of each image) and evaluates. When it evaluates the next position, it will return to block 202. If the answer to block 204 is no, then the algorithm proceeds to block 210 where it is determined whether or not the image position is within the compromised phase region. If the answer is yes, then an image is generated at the compromised phase as shown in block 212. The algorithm then proceeds to block 208 as discussed above. If the answer to block 210 is no, then the algorithm proceeds to block 214 where an ungated image is generated. It should be noted that the protocol or algorithm 200 is designed to avoid ungated images, and such an ungated image is produced only as a last resort. After block 214, the algorithm proceeds to block 208 as discussed above.

This revised cardiac reconstruction algorithm allows physicians to compromise the cardiac phase of the resulting images in order to prescribe scans at higher pitches and therefore reduce dose to the patient. The physician can enter the cardiac phase he would like to recon images at (i.e. 75% R-to-R) and he can also enter in what R-to-R percentage he is willing to compromise (i.e. 5%). When an operator specifies, for example, 75% as a phase location it is 75% of the R-to-R peak distance which is a point in time, t. To reconstruct images at t it is necessary to use information from a halfscan's worth of data (180 degrees plus a fan angle) to reconstruct each image. Therefore, at that time t, images will be reconstructed at t using data from t plus or minus ½ *halfscan's worth of data which is how the height for each reconstruction window is acquired. If there is 75% plus/minus 10% then the algorithm will start with a t that can be much higher or lower which corresponds to the "tails" on each reconstruction window. This phase compromise allows the image reconstruction algorithm to reconstruct images from multiple phases (i.e. 70% to 80%) however the algorithm will recon all images as close to the desired or "primary" phase that the physician entered (i.e. 75%) as possible. By prescribing the primary phase value and phase compromise value prospectively (prior or during the scan), the physician can use the extended cardiac reconstruction window provided by the new algorithm to increase the pitch of the scan and decrease patient dose. Dose savings can be as high as 50% or greater. Examples of possible clinical applications for the algorithm include, but are not limited to, imaging cardiac bypasses and arterial stents at 75% R-to-R with a 5% phase compromise, imaging the right atrium for atrial flutter studies at 45% R-to-R and 10% phase compromise, and imaging the aorta or lung at 75% R-to-R with 15% phase compromise. Other applications are within the scope of this invention as well.

Thus, a method and system is described which may decreases the dose to the patient for certain applications. The algorithm currently being used is not optimized for certain applications such as cardiovascular, atrial, or even lung imaging. The proposed algorithm is optimized to decrease scan time, reduce patient dose, and generate better images where there are gaps in z-coverage. The algorithm is also optimized to image cardiac regions that have small amounts of motion such as vascular, atrial, and even lung studies.

The algorithm utilizes an approach to increasing the pitch for cardiac helical scans which dramatically increases scan pitch and reduces patient dose without significant forfeits in image quality. This algorithm is unique in that it is designed for high motion structures. Even the current segmented reconstruction protocol caps the pitch at a certain heart rate so that multi-sector imaging such as Burst (multi-sector reconstruction) by GE Medical Systems may be applied retrospectively (after the scan). Since physicians studying this anatomy may not require the increased temporal resolution that one receives from using applications such as Burst or Burst Plus algorithms from GE Medical Systems, this algorithm offers them a dose savings by increasing scan pitch and gives them an optimized segment recon. Images are combined from multiple phases to prospectively increase the coverage of each recon window. Allowing the physician to enter in the percentage of phase R-to-R accuracy he is willing to compromise, allows for much increased pitch. The algorithm first reconstructs images at the primary phase, which is the phase that is requested prior to scanning, and then only reconstructs images at a compromised phase if necessary. This means that the majority of images are at the same phase with only a small amount of images being reconstructed at different, "compromised" phases. By compromising phase, the algorithm may significantly increase the scan pitch and thereby reduce the dose to the patient without making significant sacrifices to image quality. Compromising phase location also removes the necessity to generate ungated images that often have poor image quality. While there is a possibility that ungated images are generated, patient protocol must be designed to avoid this. Thus, the proposed high pitch cardiac helical algorithm provides a unique and effective solution to multiple problems in cardiac imaging.

It should be noted that the methods and algorithm described above may be employed within the imaging system 10 shown in FIGS. 3 and 4 or within a signal processor associated with a computer such as shown by item 36 in FIG. 4, and in particular, may be stored within a memory processed by a processing circuit in the processor. It is further within the scope of this invention that the disclosed methods may be embodied in the form of any computer-implemented processes and apparatuses for practicing those processes The present invention can also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. The present invention can also be embodied in the form of computer program code, for example, whether stored in a storage medium, loaded into and/or executed by a computer, or as data signal transmitted whether a modulated carrier wave or not, over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

What is claimed is:

1. A method of reconstructing cardiac images comprising:
   receiving information selecting a primary phase within a cardiac cycle;
   receiving information selecting a phase compromise value;
   calculating compromised phase regions using the phase compromise value;
   determining whether an image position is within the primary phase;
   generating an image at the primary phase if the image position is within the primary phase; and,
   generating an image at a compromised phase if the image position is not within the primary phase but is within the compromised phase regions.

2. The method of claim 1 wherein calculating the compromised phase regions compromises adding the phase compromise value to the primary phase and subtracting the phase compromise value from the primary phase.

3. The method of claim 1 further comprising calculating left and right edge locations of the primary phase.

4. The method of claim 3 wherein generating an image at the primary phase if the image position is within the primary phase comprises determining if the image position is between the left and right edge locations.

5. The method of claim 1 further comprising generating an ungated image if the image location is not within the primary phase and not within the compromised phase regions.

6. The method of claim 1 further comprising evaluating next image position subsequent to generating an image.

7. The method of claim 1 further comprising calculating center view location of the primary phase.

8. The method of claim 1 wherein receiving information comprises accepting operator input.

9. The method of claim 1 further comprising selecting a pitch higher than a pitch used for reconstructing images without compromised phase regions.

10. The method of claim 1 further comprising helically scanning an object to be imaged with a CT imaging system having a moving radiation source.

11. A computed tomographic imaging system for reconstructing cardiac images,
    said imaging system comprising a plurality of detector rows and a rotating gantry, and said imaging system being configured to:
    scan a patient at a selected helical scanning pitch;
    acquire projection data of the patient, including the patient's heart, from the plurality of detector rows;
    accept a primary phase of a cardiac cycle of the patient for image reconstruction where the heart is more motionless than at other portions of the cardiac cycle;
    calculate a compromised phase; and,
    reconstruct images at the primary phase when the image locations are within the primary phase, and reconstruct images at the compromised phase if position of the image locations is not within the primary phase but is within the compromised phase.

12. The imaging system of claim 11 wherein said imaging system is configured to scan at a helical scanning pitch which increases in relation to increasing heart rate.

13. The imaging system of claim 11 wherein said imaging system is configured to calculate a plurality of compromised phases.

14. The imaging system of claim 11 wherein images are reconstructed at the compromised phase only if images cannot be reconstructed at the primary phase.

15. The imaging system of claim 11 wherein said imaging system is configured to accept a primary phase in terms of a percentage from a first R peak of a cardiac cycle to a second R peak of a cardiac cycle and to calculate a compromised phase in terms of an R-to-R percentage that an operator is willing to compromise.

16. The imaging system of claim 15 wherein said imaging system is configured to calculate a plurality of compromised phases, some of said plurality of compromised phases beginning before said primary phase, and some of said plurality of compromised phases ending after said primary phase.

17. A storage medium encoded with machine-readable computer program code for reconstructing cardiac images, the storage medium including instructions for causing a computer to implement a method comprising:
   receiving information selecting a primary phase within a cardiac cycle;
   receiving information selecting a phase compromise value;
   calculating compromised phase regions using the phase compromise value;
   determining whether an image position is within the primary phase;
   generating an image at the primary phase if the image position is within the primary phase; and,
   generating an image at a compromised phase if the image position is not within the primary phase but is within the compromised phase regions.

18. A computed tomographic imaging system for reconstructing cardiac images,
   said imaging system comprising a plurality of detector rows and a rotating gantry, said imaging system including:
   means for scanning a patient at a selected helical scanning pitch;
   means for acquiring projection data of the patient, including the patient's heart, from the plurality of detector rows;
   means for accepting a primary phase of a cardiac cycle of the patient for image reconstruction where the heart is more motionless than at other portions of the cardiac cycle;
   means for calculating a compromised phase; and,
   means for reconstructing images at the primary phase when the image locations are within the primary phase, and means for reconstructing images at the compromised phase if position of the image locations is not within the primary phase but is within the compromised phase.

19. The imaging system of claim 18 wherein the means for reconstructing images includes an image reconstructor.

20. The imaging system of claim 18 wherein the means for calculating a comprised phase includes a computer.

21. The imaging system of claim 18 wherein the means for scanning includes a computed tomography scanner.

22. A method of reconstructing cardiac images using a computed tomographic imaging system, said method comprising:
   receiving information selecting a primary phase within a cardiac cycle;
   receiving information selecting a phase compromise value;
   calculating compromised phase regions using the phase compromise value;
   selecting a helical scanning pitch for scanning a patient;
   scanning the patient, including the patient's heart, with a computed tomographic imaging system having a plurality of detector rows and a rotating gantry to acquire projection data from the plurality of detector rows;
   determining whether an image position is within the primary phase;
   generating an image at the primary phase if the image position is within the primary phase; and,
   generating an image at a compromised phase if the image position is not within the primary phase but is within the compromised phase regions.

23. A method of reducing radiation dose delivered to a patient during a computed tomographic imaging session, the method comprising:
   increasing a helical scanning pitch for scanning a patient; and,
   extending a reconstruction window around a primary phase for image reconstruction.

24. The method of claim 23 wherein increasing a helical scanning pitch comprising increasing the pitch for increased heart rates.

25. The method of claim 23 wherein extending a reconstruction window comprising selecting a primary phase, selecting a phase compromise value, and calculating comprised phase region at beginning and end locations of the primary phase.

* * * * *